(12) United States Patent
Li et al.

(10) Patent No.: US 11,167,280 B2
(45) Date of Patent: Nov. 9, 2021

(54) CATALYST FOR PREPARING α-PHENYLETHANOL BY HYDROGENATION OF ACETOPHENONE, PREPARATION METHOD THEREOF AND APPLICATION THEREOF

(71) Applicant: Wanhua Chemical Group Co., Ltd., Shandong (CN)

(72) Inventors: Zuojin Li, Shandong (CN); Haibo Yu, Shandong (CN); Jishan Zhan, Shandong (CN); Yu Sha, Shandong (CN); Naibo Chu, Shandong (CN); Yuan Li, Shandong (CN); Weiqi Hua, Shandong (CN)

(73) Assignee: Wanhua Chemical Group Co., Ltd.

( * ) Notice: Subject to any disclaimer, the term of this patent is extended or adjusted under 35 U.S.C. 154(b) by 0 days.

(21) Appl. No.: 16/763,865

(22) PCT Filed: Jun. 29, 2018

(86) PCT No.: PCT/CN2018/093616
§ 371 (c)(1),
(2) Date: May 13, 2020

(87) PCT Pub. No.: WO2019/109629
PCT Pub. Date: Jun. 13, 2019

(65) Prior Publication Data
US 2020/0282388 A1 Sep. 10, 2020

(30) Foreign Application Priority Data
Dec. 6, 2017 (CN) .......................... 201711277978.2

(51) Int. Cl.
| | | |
|---|---|---|
| *B01J 37/00* | (2006.01) |
| *B01J 23/00* | (2006.01) |
| *B01J 23/83* | (2006.01) |
| *B01J 37/03* | (2006.01) |
| *B01J 37/08* | (2006.01) |
| *B01J 37/18* | (2006.01) |
| *C07C 29/145* | (2006.01) |
| *B01J 35/00* | (2006.01) |

(52) U.S. Cl.
CPC ......... *B01J 37/0018* (2013.01); *B01J 23/002* (2013.01); *B01J 23/83* (2013.01); *B01J 37/031* (2013.01); *B01J 37/082* (2013.01); *B01J 37/18* (2013.01); *C07C 29/145* (2013.01); *B01J 35/0093* (2013.01)

(58) Field of Classification Search
CPC ...... B01J 23/002; B01J 23/83; B01J 35/0093; B01J 37/0018; B01J 37/0063; B01J 37/03; B01J 37/031; B01J 37/082; B01J 37/18; B01J 2523/00; C07C 29/145
See application file for complete search history.

(56) References Cited

U.S. PATENT DOCUMENTS

| | | |
|---|---|---|
| 3,927,121 A | 12/1975 | Grane et al. |
| 4,996,374 A | 2/1991 | Lin et al. |
| 6,528,034 B1 | 3/2003 | Pinnavaia et al. |
| 2001/0016671 A1 | 8/2001 | Oku et al. |

FOREIGN PATENT DOCUMENTS

| | | |
|---|---|---|
| CN | 1315226 A | 10/2001 |
| CN | 1557545 A | 12/2004 |
| CN | 1911883 A | 2/2007 |
| CN | 102327774 A | 1/2012 |
| CN | 105013501 A | 11/2015 |
| CN | 107115895 A | 9/2017 |
| CN | 108043414 A | 5/2018 |
| DE | 3933661 A1 | 4/1991 |
| EP | 0714877 B1 | 10/1999 |
| JP | H05192588 A | 8/1993 |
| JP | H09136849 A | 5/1997 |

(Continued)

OTHER PUBLICATIONS

Derwent abstract of Chen et al (CN 106345461), Jan. 25, 2017.*
International Search Report for Application No. PCT/CN2018/093616, dated Sep. 12, 2018, pp. 1-2.
Chen, Q. et al., "Synthesis of monodispersed mesoporous silica spheres (MMSSs) with controlled particle size using gemini surfactant", Microporous and Mesoporous Materials, Aug. 2009, pp. 203-212, vol. 128, Elsevier, XP028748355.
Extended European Search Report including Written Opinion for Application No. 18886984.6 dated Aug. 20, 2021, pp. 1-10.
Li, W. et al., "Synthesis and characterization of ordered mesoporous silica using rosin-based Gemini surfactants", Journal of Material Science, Oct. 2017, pp. 2434-2442, vol. 53, Springer Science Business Media LLC. XP036380310.

*Primary Examiner* — Brian A McCaig
(74) *Attorney, Agent, or Firm* — Lerner, David, Littenberg, Krumholz & Mentlik, LLP

(57) ABSTRACT

Disclosed is catalyst preparation method for liquid phase hydrogenation of acetophenone in preparation of α-phenylethanol. The method includes adding water, small alcohol, Gemini surfactant and organic pore-forming agent to reactor. Then adding silica sol and stirring to prepare aqueous dispersion of silica sol; preparing alkaline precipitant and mixed solution containing salts of copper containing compound, zinc containing compound, rare-earth metal containing compound and alkaline-earth metal containing compound, adding alkaline precipitant and mixed solution together to aqueous dispersion, followed by precipitation, ageing, filtration, washing, drying, calcination and molding to obtain catalyst. By using silica sol and silicate as composite silicon source, adding organic pore-forming agent before precipitation process, modifying catalyst by Zn, rare-earth metal and alkaline earth metal, when using liquid phase hydrogenation of acetophenone to prepare α-phenylethanol, catalyst has high activity and good selectivity, and effectively improves the catalyst's liquid resistance, has high strength and good stability.

20 Claims, No Drawings

(56) References Cited

FOREIGN PATENT DOCUMENTS

WO 2016059431 A1 4/2016
WO 2016198379 A1 12/2016

* cited by examiner

CATALYST FOR PREPARING α-PHENYLETHANOL BY HYDROGENATION OF ACETOPHENONE, PREPARATION METHOD THEREOF AND APPLICATION THEREOF

CROSS REFERENCE TO RELATED APPLICATIONS

The present application is a national phase entry under 35 U.S.C. § 371 of International Application No. PCT/CN2018/093616, filed Jun. 29, 2018, which claims priority from Chinese Patent Application No. 201711277978.2 filed Dec. 6, 2017, all of which are hereby incorporated herein by reference.

TECHNICAL FIELD

The invention belongs to the technical field of catalytic hydrogenation, specifically relates to a catalyst for liquid phase hydrogenation of acetophenone to produce α-phenylethanol, and relates to the preparation method and use of the catalyst.

BACKGROUND

α-Phenylethanol is an important chemical intermediate, which is widely used in industries such as medicine, perfume manufacturing, cosmetics, food and fine chemical. The existing methods for synthesizing α-phenylethanol mainly include microbial fermentation method and acetophenone reduction/catalytic hydrogenation method.

The microbial fermentation method generally uses phenylalanine and fluorophenylalanine as raw materials, and produces α-phenylethanol through microbial fermentation transformation. The raw materials used in the microbial method are expensive and the production cost is high. Currently, acetophenone hydrogenation method is generally used in the production of α-phenylethanol in industry. This method has the advantages of low production cost, less by-products, high product yield and high product purity, and the method is suitable for large-scale production of α-phenylethanol.

The acetophenone hydrogenation catalysts mainly include noble metal (such as platinum and palladium) catalysts, nickel-based catalysts, and copper-based catalysts. Noble metal catalysts and nickel-based catalysts have high costs, are liable to cause aromatic ring saturation and phenylethanol hydrogenolysis, and have poor selectivity to α-phenylethanol. Compared with noble metal catalysts and nickel-based catalysts, when using for acetophenone hydrogenation reaction, copper-based catalysts have the advantages of high activity, high selectivity and low cost.

Catalysts for the hydrogenation of acetophenone to produce α-phenylethanol are reported in many patent documents. In CN1557545A, a Ni—Sn—B/$SiO_2$ catalyst was prepared by impregnation method, after low-temperature calcination, reduction was performed using $KBH_4$ as a reducing agent. In the catalytic reaction of the catalyst, the maximum selectivity to phenylethanol is up to 97.5%, but the interaction force between the active component Ni and the carrier $SiO_2$ is weak and the active component Ni is easy to lose.

U.S. Pat. No. 4,996,374 discloses a Pd—C catalyst, but the stability of the catalyst is poor, and it is necessary to continuously increase the reaction temperature when recycled. CN1315226A discloses a reduction treated copper-based catalyst and a method for preparing α-phenylethanol using the catalyst, but the catalyst requires a liquid phase reduction method to improve the stability thereof, which is complicated in process and costly. CN1911883A discloses a method for preparing α-phenylethanol using Raney nickel as a catalyst, but there is a large amount of aromatic ring hydrogenation product α-cyclohexylethanol in the acetophenone hydrogenation product, the selectivity to α-phenylethanol is low.

EP0714877B1 uses carbonates of alkali metal and/or alkaline-earth metal to modify the copper-silicon catalyst, which significantly inhibits the formation of by-product ethylbenzene. However, the silicon source is added in the form of fumed silica or diatomaceous earth, which is detrimental to the enhancement of the interaction between the active component and the carrier, therefore detrimental to the strength of the catalyst.

Some silicon sources in the catalyst of WO2016198379 are added in the form of silica sol during extrusion molding, which cannot effectively disperse the active component copper. None of the above-mentioned publications mentions the dispersing and stabilizing effects of the additives on the active components, the mechanical stability during use and strength after use of the molded catalysts.

Since the acetophenone hydrogenation process is extremely prone to the side reactions of α-phenylethanol hydrogenolysis/dehydration to form ethylbenzene/styrene, the reaction rates of hydrogenolysis and dehydration increase rapidly with the increase of the reaction temperature. In order to improve the selectivity of the acetophenone hydrogenation process, the liquid phase hydrogenation reaction at a lower temperature is usually selected. Therefore, the acetophenone hydrogenation catalyst is required to have good liquid resistance, weak acidity and good activity at low temperature.

In the prior art, the copper-based catalysts for liquid phase hydrogenation reaction are not only subjected to various internal or external forces during storage/charging/reduction/reaction processes, but also subjected to significant decrease in strength during actual use due to liquid soaking, swelling and so on, which cause the catalyst to be easily crushed and powdered in the liquid phase hydrogenation system, threatening the stable operation of industrial units and affecting the life of the catalyst.

At present, the copper-based catalysts for acetophenone hydrogenation to produce α-phenylethanol prepared by the precipitation method usually have problems such as low dispersity of active component copper, strong acidity and weak interaction between the carrier and the active component, leading to low conversion rate of acetophenone, large amount of by-products such as ethylbenzene, poor selectivity to phenylethanol and poor catalyst strength. Therefore, improving the dispersity of the active component copper and the mass transfer performance of the catalyst, suppressing the acidity of the catalyst, and improving the liquid resistance of the catalyst are of great significance for the preparation of acetophenone hydrogenation catalyst with high activity, high selectivity and high liquid resistance.

SUMMARY

The purposes of the present invention is to provide a preparation method of a catalyst for producing α-phenylethanol by liquid phase hydrogenation of acetophenone, and a prepared catalyst. The catalyst prepared by the method significantly suppresses side reactions such as hydrogenolysis, and has high catalyst activity and high selectivity; at the same time, the catalyst has excellent liquid resistance and has high strength after reduction and liquid phase hydrogenation reaction.

To achieve one aspect of the above purposes, the present invention adopts the following technical solutions:

a preparation method for a hydrogenation catalyst, comprising the following steps:

(1) adding deionized water, a small molecule alcohol, a Gemini surfactant, and an organic pore-forming agent to a reactor, followed by adding a silica sol and stirring the mixture well to prepare an aqueous dispersion of silica sol containing the small molecule alcohol, the Gemini surfactant and the organic pore-forming agent;

(2) dissolving a salt of a copper containing compound, a salt of a zinc containing compound, a salt of a rare-earth metal containing compound and a salt of an alkaline-earth metal containing compound in water to prepare a solution of mixed salt; dissolving a silicon containing alkaline precipitant and a silicon free alkaline precipitant in water to prepare an aqueous solution of alkaline precipitant; adding the solution of mixed salt and the aqueous solution of alkaline precipitant together to the aqueous dispersion of silica sol for reaction, with the pH of the reaction system during the reaction process being controlled at 5.0-9.0, and followed by aging to obtain a slurry;

(3) filtering and washing the slurry to obtain a filter cake;

(4) drying, calcining and molding the filter cake to obtain the catalyst.

In the present invention, step (1) aims at mixing deionized water, a small molecule alcohol, a Gemini surfactant, an organic pore-forming agent and a silica sol well to prepare an aqueous dispersion of silica sol containing the small molecule alcohol, the Gemini surfactant and the organic pore-forming agent, wherein, the organic pore-forming agent is preferably selected from one or more of PMMA, microcrystalline cellulose and methyl cellulose; the organic pore-forming agent is added during the preparation process to reduce the diffusion resistance in the raw materials and the product, and therefore effectively improve the activity and selectivity of the catalyst.

According to the preparation method of the present invention, preferably, the particle size of the organic pore-forming agent is <100 μm, more preferably 1-80 μm, and still more preferably 3-30 μm, such as 5, 10, 15, 20, or 25 μm. Keeping the particle size of the organic pore-forming agent within a suitable range will be conducive to further improving the diffusion mass transfer effect of the raw materials and the product. If the particle size is too large, it is not conducive to playing an effective role in improving the mass transfer performance; if the particle size is too small, it is not conducive to improving the mass transfer performance too.

According to the preparation method of the present invention, preferably, the amount of the organic pore-forming agent accounts for 0.5-20 wt %, more preferably 1-10 wt % and still more preferably 2-5 wt % of the total weight of the catalyst. Keeping the amount of organic pore-forming agent in a suitable range will be conducive to minimizing the impact on the strength of the catalyst on the premise of achieving good mass transfer performance. If the amount of organic pore-forming agent is too small, it is not conducive to playing an effective role in improving the mass transfer performance; if the amount of organic pore-forming agent is too much, the mechanical strength of the catalyst will be affected.

In the present invention, the total amount of silicon in the catalyst is introduced by the silica sol and the silicon containing alkaline precipitant together. Preferably, the amount of silicon introduced by the silica sol accounts for 30-70 wt %, more preferably 35-65 wt %, still more preferably 40-60 wt %, such as 50 wt % of the total amount of silicon in the catalyst. Studies have found that compared with the use of a single silicon source, using a highly dispersed silica sol and a silicon containing alkaline precipitant as a composite silicon source, the prepared catalyst is not only highly active but also has high strength. Preferably, the silica sol is an alkaline silica sol, and the pH value is 8.0-10.0.

In the present invention, the small molecular alcohol refers to an alcohol having a molecular weight of not more than 400, such as a small molecular saturated monohydric alcohol having a molecular weight of not more than 400. According to the preparation method of the present invention, preferably, the mass ratio of the small molecule alcohol to deionized water is 1:20 to 1:10, such as 1:18, 1:15, or 1:12; further preferably, the small molecule alcohol in step (1) is one or more of methanol, ethanol, propanol and butanol.

In the present invention, the used Gemini surfactant is well known in the art, and it is a new surfactant that connects two or more traditional surfactant molecules at a hydrophilic group or near a hydrophilic group through a linking group. The Gemini surfactant has at least two hydrophobic hydrocarbon chains, two polar head groups and a linking group; the linking group can be long, short, rigid, flexible, polar or non-polar; the Gemini surfactant can be divided into anionic-type, cationic-type, nonionic-type and zwitterionic-type Gemini surfactants depending on whether the polar head group is cationic, anionic or nonionic; the Gemini surfactant can be divided into symmetric Gemini surfactant and asymmetric Gemini surfactant based on the bipolar head group and hydrophobic chain structure. According to the preparation method of the present invention, preferably, the Gemini surfactant in the step (1) is added in an amount of 0.1%-1% of the total mass of the deionized water and the small molecule organic alcohol. The specific type of Gemini surfactant used in the present invention is not particularly limited. In some preferred embodiments, the Gemini surfactant is a bromide having a structure of $C_{m-n-m}$, wherein m is preferably 12, 14 or 16, and n is preferably 2, 3, 6, 8 or 10. The used Gemini surfactants can be obtained from the corresponding reagents available on the market, for example, which can be Gemini surfactants having a structure of $C_{16-6-16}$, $C_{12-10-12}$, $C_{14-8-14}$, $C_{12-8-12}$ or $C_{14-10-14}$, or Gemini surfactants having a structure of $C_{16-2-16}$, $C_{12-3-12}$, $C_{14-2-14}$ or $C_{12-3-12}$, etc., purchased from Henan Daochun Chemical Co., Ltd.

Studies have found that in the present invention, by adding Gemini surfactant and small molecular alcohol to modify the silica sol, the dispersity of the silica sol is improved, such that the active component copper has higher dispersity, and the catalyst activity is improved. Meanwhile, the Gemini surfactant can further cooperate with the organic pore-forming agent to promote the formation of mesoporous structure and improve the mass transfer performance of the catalyst.

In the present invention, the precipitant refers to substance that can react with the metal cation in the solution of mixed salt to form corresponding precipitate. The purpose of step (2) is to prepare a solution of mixed salt and an aqueous solution of alkaline precipitant, and add the two together to the aqueous dispersion of silica sol, so that the mixed salt become corresponding precipitate in the aqueous dispersion of silica sol containing the organic pore-forming agent. Studies have found that by dispersing the pore-forming agent in the silica sol in advance, and then forming a precipitate in the silica sol, it is beneficial to the better dispersion of the pore-forming agent in the precipitate.

According to the preparation method of the present invention, preferably, the silicon containing alkaline precipitant is a water soluble silicate, preferably one or two of sodium silicate and potassium silicate; the silicon free alkaline precipitant is one or more of potassium carbonate, sodium bicarbonate, potassium bicarbonate, sodium hydroxide, potassium hydroxide, ammonium carbonate, ammonium bicarbonate, carbamide and ammonia water.

Those skilled in the art understand that in the present invention, each metal salt forming the solution of mixed salt is a soluble salt of the corresponding metal. According to the preparation method of the present invention, preferably, the salt of the copper containing compound is one or more of copper nitrate, copper chloride and copper acetate; the salt of the zinc containing compound is one or more of zinc nitrate, zinc chloride and zinc acetate; the salt of the rare-earth metal compound is one or more of nitrate, chloride and acetate; the salt of the alkaline-earth metal compound is one or more of nitrate, chloride and acetate.

In the present invention, Zn and Cu can form a "solid solution" during the preparation process, which can effectively promote the dispersion of the active component copper in the catalyst; the addition of a rare-earth metal also plays a role in improving the dispersity of the copper in the catalyst and the stability of the catalyst, preferably, the rare-earth metal is lanthanum and/or cerium; the addition of an alkaline-earth metal significantly inhibits the acidity of the catalyst, can effectively inhibit the formation of ethylbenzene, and improves the reaction selectivity, preferably, the alkaline-earth metal is one or two or more of magnesium, calcium and barium. Those skilled in the art understand that each metal component is added in an amount such that the oxide in the prepared catalyst corresponding to each metal component reaches its target amount. In some preferred embodiments, based on the total weight of the catalyst, the prepared catalyst contains 20-65 wt % of copper oxide, 15-50 wt % of silicon oxide, 2-25 wt % of zinc oxide, 0.1-5 wt % of rare-earth metal oxide and 0.5-15 wt % of alkaline-earth metal oxide; more preferably, the prepared catalyst contains 40-63 wt % of copper oxide, 20-45 wt % of silicon oxide, 5-20 wt % of zinc oxide, 0.2-3 wt % of rare-earth metal oxide and 0.5-10 wt % of alkaline-earth metal oxide; still more preferably, the prepared catalyst contains 42-60 wt % of copper oxide, 22-40 wt % of silicon oxide, 10-18 wt % of zinc oxide, 0.5-2 wt % of rare-earth metal oxide and 1-5 wt % of alkaline-earth metal oxide.

In step (2), the pH of the reaction system during the reaction process is controlled to 5.0-9.0, such as 5.5-8.0, and then the system is aged to obtain a slurry; preferably, the temperature of the reaction process and the aging process is controlled to 60-90° C., such as 70 or 80° C. The specific process for forming a precipitate through a reaction and the precipitate aging process are well known in the art, for example, the reaction process for forming a precipitate can be completed within 1-3 hours, and then aging for another 1-3 hours.

In the present invention, the purpose of step (3) is to filter and wash the slurry to obtain a filter cake; the filtering and washing processes can all adopt the filtering and washing processes commonly used in the art, which are all processes commonly used for treating catalysts in the art. In step (4), the drying, calcining, and molding processes for the filter cake are also commonly used processes for treating catalysts in the art; in one embodiment, the calcining temperature is 300-700° C., such as 400, 500, or 600° C.; the calcining time is 4-12h, such as 6, 8 or 10h; the molding may be tablet molding and the like.

To achieve one aspect of the above purposes, the present invention also provides a catalyst prepared according to the above preparation method.

According to the preparation method of the present invention, preferably, based on the total weight of the catalyst, the catalyst includes 20-65 wt % of copper oxide, 15-50 wt % of silicon oxide, 2-25 wt % of zinc oxide, 0.1-5 wt % of rare-earth metal oxide and 0.5-15 wt % of alkaline-earth metal oxide; more preferably, the catalyst includes 40-63 wt % of copper oxide, 20-45 wt % of silicon oxide, 5-20 wt % of zinc oxide, 0.2-3 wt % of rare-earth metal oxide and 0.5-10 wt % of alkaline-earth metal oxide; still more preferably, the catalyst includes 42-60 wt %, such as 50 wt % of copper oxide, 22-40 wt %, such as 30 wt % of silicon oxide, 10-18 wt %, such as 15 wt % of zinc oxide, 0.5-2 wt %, such as 1 wt % or 1.5 wt % of rare-earth metal oxide, and 1-5 wt %, such as 2 wt % or 3 wt % of alkaline-earth metal oxide.

The invention also provides use of the above catalyst in the liquid phase hydrogenation of acetophenone to produce α-phenylethanol.

Those skilled in the art understand that the catalyst needs to be reduced and activated before having corresponding catalytic activity for the hydrogenation of acetophenone to produce α-phenylethanol.

In a preferred embodiment, the method for reducing and activating the catalyst according to the present invention comprises: maintaining a volume space velocity of a mixed gas of hydrogen and nitrogen of 300-1000 $h^{-1}$, and preferably first increasing the temperature of the reactor to 160-180° C., keeping the temperature constant for 1-2 h and removing the physical water adsorbed by the catalyst, and followed by introducing a mixed gas of hydrogen and nitrogen with a volume fraction of $H_2$ not more than 10 v %, such as (5 v %±2 v %), to pre-reduce the catalyst for at least 0.5 h, such as 1 h, 1.5h or 2 h, followed by gradually increasing the proportion of hydrogen in the mixed gas of hydrogen and nitrogen, for example, gradually increasing the proportion of hydrogen to 10 v %, 20 v %, 50 v %, 100 v % and controlling the hot spot temperature of the catalyst bed in this process to be not exceed 220° C., and finally raising the temperature to 200-220° C. and reducing in pure hydrogen atmosphere for 2-5 h, such as 3h or 4 h, to obtain an activated catalyst.

In a preferred embodiment, when the obtained reduced catalyst is used for the hydrogenation of acetophenone to produce α-phenylethanol, the reaction pressure is 2.5-5 MPa (relative pressure), such as 3-5 MPa (relative pressure), and the reaction temperature is 70-140° C., such as 120-140° C., the $H_2$/ACP (acetophenone) molar ratio is 2-20:1, such as 5:1, 10:1 or 15:1, and the amount of the catalyst is 0.2-0.6 $g_{ACP} \cdot g_{cat}^{-1} \cdot h^{-1}$.

Compared with the prior art, in the process of the liquid phase hydrogenation of acetophenone to produce α-phenylethanol using the catalyst prepared by the present invention, the catalyst has evenly distributed active components, high dispersity of copper, smooth catalyst pores, weak acidity, excellent activity, excellent selectivity and excellent mechanical strength.

In addition, as to the catalyst prepared by the method of the present invention, the addition of a pore-forming agent can effectively improve the mass transfer performance of the catalyst and is beneficial to the improvement of the catalyst activity; the use of a composite silicon source can obtain a catalyst for liquid phase hydrogenation with high activity and good mechanical strength; the addition of Zn, rare-earth, and alkaline-earth metals in the catalyst is conducive to improving the dispersity of the active component Cu, inhibiting the acidity of the catalyst and improving the activity and selectivity of the catalyst.

EMBODIMENT

The method of the present invention is described in detail below with reference to the examples, but the present invention is not limited thereto.

The side pressure strength of the catalyst was measured using a particle strength tester, and the used catalyst was immersed and protected with ethylbenzene to prevent the catalyst from being oxidized. The side pressure strengths of 40 pellets of the reacted catalyst were measured and the average value was taken.

The copper ion content in the hydrogenation solution was measured by inductively coupled plasma-atomic emission spectrometry (ICP).

Unless otherwise specified, the reagents used below are analytically pure and are commercially available products.

Example 1

Into a reactor, 200 g of water, 10 g of methanol, 4.0 g of PMMA with a particle size of 10-30 μm, and 2.0 g of Gemini surfactant with a structure of $C_{16-6-16}$ (purchased from Henan Daochun Chemical Co., Ltd) were added and mixed evenly, and then 120.0 g of alkaline silica sol with a concentration of 30 wt % and a pH value of 9 was added and stirred well. 332.2 g of copper nitrate, 73.1 g of zinc nitrate, 21.3 g of lanthanum nitrate, 12.7 g of magnesium nitrate were dissolved in 1.5 kg of water to prepare an aqueous solution of mixed salt, 113.5 g of sodium silicate and 142.5 g of sodium carbonate were dissolved in water to prepare a precipitant solution, the two solutions were heated to 70° C. respectively. The coprecipitation method was used, the two solutions were added dropwise into the reactor at the same time, and the temperature in the reactor during the precipitation process was controlled at 70° C., the pH of the system was controlled at 7.0 and the reaction time was 1 h. After the addition of the two solutions was completed, the pH of the system was adjusted to >7.5 using a solution with 10 wt % sodium carbonate, the system was aged at 75° C. for 3h, then filtered, washed, the filter cake was dried at 110° C. for 12 h, calcined at 350° C. for 8h, then mixed with 1.5 wt % (powder mass) of graphite and pressed into a 3×3 mm cylinder (3 mm in diameter and 3 mm in height) catalyst, about 200 g of Catalyst A was obtained. Based on the oxides, the catalyst contains 55% of copper oxide, 30% of silicon oxide, 10% of zinc oxide, 1% of lanthanum oxide and 4% of magnesium oxide.

Catalyst reduction: the catalyst A was charged in a fixed-bed hydrogenation reactor, and the charging amount of the catalyst was 100 ml. The catalyst was reduced under a mixed gas of nitrogen and hydrogen before use. During the reduction, the volume space velocity of the mixed gas was maintained at 300h$^{-1}$. The temperature of the reactor was first raised to 160° C. and the temperature was maintained for 2h to remove the physical water adsorbed by the catalyst, and then a mixed gas of nitrogen and hydrogen with a $H_2$ volume fraction of 5 v % was added to pre-reduce the catalyst for 1 h. Then the proportion of hydrogen in the mixed gas of nitrogen and hydrogen was gradually increased to 10 v %, 20 v %, 50 v % and 100 v %, the hot spot temperature of the catalyst bed in this process was controlled not to exceed 220° C., finally the temperature was raised to 220° C. and the catalyst was reduced under a pure hydrogen atmosphere for 3h.

The hydrogenation raw material was an ethylbenzene solution with 15 wt % acetophenone, and the reaction was carried out under the conditions of a pressure of 2.5 Mpa, a temperature of 70° C., a molar ratio of $H_2$/ketone of 5:1, and a catalyst throughput of 0.3 $g_{ACP}/g_{cat}$/h. The hydrogenation solution was taken every 24h and the copper ion content in the hydrogenation solution was measured. After 100 hours of reaction, the catalyst was removed from the reactor and the catalyst was sieved with a stainless steel sample sieve with a diameter of 2 mm, and the ratio of the mass of the catalyst particles with a particle size of <1 mm to the total mass of the catalyst was calculated and used as the catalyst damage rate. A particle strength tester was used to determine the side pressure strength of the catalyst after the reaction. The results of the hydrogenation reaction and the average copper ion content in the hydrogenation solution are shown in Table 1. See Table 2 for comparison of the catalyst before and after the reaction.

Example 2

Into a reactor, 200 g of water, 15 g of ethanol, 6.0 g of microcrystalline cellulose with a particle size of 5-30 μm, and 0.5 g of Gemini surfactant with a structure of $C_{12-10-12}$ (purchased from Henan Daochun Chemical Co., Ltd.) were added, and then 61.3 g of silica sol with a concentration of 30 wt % was added and stirred well. 362.4 g of copper nitrate, 87.7 g of zinc nitrate, 22.7 g of cerium nitrate, 4.21 g of calcium nitrate were dissolved in 1.45 kg of water to prepare an aqueous solution of mixed salt, 130.5 g of sodium silicate and 149.0 g of sodium carbonate were dissolved in water to prepare a precipitant solution. The two solutions were heated to 75° C. respectively. The coprecipitation method was used, the two solutions were added dropwise into the reactor at the same time, and the temperature in the reactor during the precipitation process was controlled at 75° C., the pH of the system was controlled at 7.2 and the reaction time was 1 h. After the addition of the two solutions was completed, the pH of the system was adjusted to >7.5 using a solution with 10 wt % sodium carbonate, the system was aged at 80° C. for 3 h, then filtered, washed, the filter cake was dried at 100° C. for 24 h, calcined at 400° C. for 12 h, then mixed with 1.0 wt % (powder mass) of graphite and pressed into a 3×3 mm cylinder (3 mm in diameter and 3 mm in height) catalyst, about 200 g of Catalyst B was obtained. Based on the oxides, the catalyst contains 60% of copper oxide, 23% of silicon oxide, 12% of zinc oxide, 0.5% of cerium oxide and 4.5% of calcium oxide.

For the remaining conditions, refer to Example 1.

Example 3

Into a reactor, 200 g of water, 10 g of propanol, 10.0 g of methylcellulose with a particle size of 5-20 μm, and 1.0 g of Gemini surfactant with a structure of $C_{14-8-14}$ (purchased from Henan Daochun Chemical Co., Ltd.) were added and mixed evenly, and then 116.7 g of silica sol with a concentration of 30 wt % was added and stirred well. 302 g of copper nitrate, 87.7 g of zinc nitrate, 5.0 g of cerium nitrate, 6.8 g of barium nitrate were dissolved in 1.37 kg of water to prepare an aqueous solution of mixed salt, 198.7 g of sodium silicate and 93.6 g of sodium carbonate were dissolved in water to prepare a precipitant solution. The two solutions were heated to 80° C. respectively. The coprecipitation method was used, the two solutions were added dropwise into the reactor at the same time, and the temperature in the reactor during the precipitation process was controlled at 80° C., the pH of the system was controlled at 8.0 and the reaction time was 1 h. After the addition of the two solutions was completed, the pH of the system was adjusted to >7.3 using a solution with 10 wt % sodium carbonate, the system was aged at 85° C. for 3 h, then filtered, washed, the filter cake was dried at 120° C. for 12 h, calcined at 550° C. for 8 h, then mixed with 1.2 wt % (powder mass) of graphite and pressed into a 3×3 mm cylinder (3 mm in diameter and 3 mm in height) catalyst, about 200 g of Catalyst C was obtained. Based on the oxides, the catalyst contains 50% of copper oxide, 35% of silicon oxide, 12% of zinc oxide, 1% of cerium oxide and 2% of barium oxide.

For the remaining conditions, refer to Example 1.

Example 4

Into a reactor, 200 g of water, 20 g of butanol, 6.0 g of microcrystalline cellulose with a particle size of 3-20 μm, and 0.2 g of Gemini surfactant with a structure of $C_{12-8-12}$ (purchased from Henan Daochun Chemical Co., Ltd.) were added and mixed evenly, and then 105 g of silica sol with a concentration of 30 wt % was added and stirred well. 271.8 g of copper nitrate, 109.7 g of zinc nitrate, 10.6 g of lanthanum nitrate, 25.3 g of calcium nitrate were dissolved in 1.39 kg of water to prepare an aqueous solution of mixed salt, 182.1 g of sodium silicate and 105.6 g of sodium carbonate were dissolved in water to prepare a precipitant solution. The two solutions were heated to 60° C. respectively. The coprecipitation method was used, the two solutions were added dropwise into the reactor at the same time, and the temperature in the reactor during the precipitation process was controlled at 60° C., the pH of the system was controlled at 6.5 and the reaction time was 1 h. After the addition of the two solutions was completed, the pH of the system was adjusted to >7.2 using a solution with 10 wt % sodium carbonate, the system was aged at 70° C. for 3 h, then filtered, washed, the filter cake was dried at 100° C. for 12 h, calcined at 450° C. for 6 h, then mixed with 1.0 wt % (powder mass) of graphite and pressed into a 3×3 mm cylinder (3 mm in diameter and 3 mm in height) catalyst, about 200 g of Catalyst D was obtained. Based on the oxides, the catalyst contains 45% of copper oxide, 35% of silicon oxide, 15% of zinc oxide, 2% of lanthanum oxide and 3% of calcium oxide.

For the remaining conditions, refer to Example 1.

Example 5

Into a reactor, 200 g of water, 20 g of ethanol, 10.0 g of PMMA with a particle size of 10-30 μm, and 1.5 g of Gemini surfactant with a structure of $C_{14-10-14}$ (purchased from Henan Daochun Chemical Co., Ltd.) were added and mixed evenly, and then 177.3 g of silica sol with a concentration of 30 wt % was added and stirred well. 24.6 g of copper nitrate, 131.6 g of zinc nitrate, 7.97 g of lanthanum nitrate, 31.8 g of magnesium nitrate were dissolved in 1.65 kg of water to prepare an aqueous solution of mixed salt, 107.8 g of sodium silicate and 128.7 g of sodium carbonate were dissolved in water to prepare a precipitant solution. The two solutions were heated to 85° C. respectively. The coprecipitation method was used, the two solutions were added dropwise into the reactor at the same time, and the temperature in the reactor during the precipitation process was controlled at 85° C., the pH of the system was controlled at 7.0 and the reaction time was 1 h. After the addition of the two solutions was completed, the pH of the system was adjusted to >7.5 using a solution with 10 wt % sodium carbonate, the system was aged at 90° C. for 3 h, then filtered, washed, the filter cake was dried at 110° C. for 12 h, calcined at 650° C. for 4 h, then mixed with 1.2 wt % (powder mass) of graphite and pressed into a 3×3 mm cylinder (3 mm in diameter and 3 mm in height) catalyst, about 200 g of Catalyst E was obtained. Based on the oxides, the catalyst contains 40% of copper oxide, 38% of silicon oxide, 18% of zinc oxide, 1.5% of lanthanum oxide and 2.5% of calcium oxide.

For the remaining conditions, refer to Example 1.

Example 6

Into a reactor, 200 g of water, 15 g of methanol, 4.0 g of methylcellulose with a particle size of 3-30 μm, and 0.8 g of Gemini surfactant with a structure of $C_{12-8-12}$ (purchased from Henan Daochun Chemical Co., Ltd.) were added and mixed evenly, and then 117.3 g of silica sol with a concentration of 30 wt % was added and stirred well. 314.1 g of copper nitrate, 73.1 g of zinc nitrate, 5.0 g of cerium nitrate, 17.0 g of barium nitrate were dissolved in 1.5 kg of water to prepare an aqueous solution of mixed salt, 136.2 g of sodium silicate and 121.2 g of sodium carbonate were dissolved in water to prepare a precipitant solution. The two solutions were heated to 65° C. respectively. The coprecipitation method was used, the two solutions were added dropwise into the reactor at the same time, and the temperature in the reactor during the precipitation process was controlled at 65° C., the pH of the system was controlled at 6.8 and the reaction time was 1 h. After the addition of the two solutions was completed, the pH of the system was adjusted to >7.5 using a solution with 10 wt % sodium carbonate, the system was aged at 70° C. for 3 h, then filtered, washed, the filter cake was dried at 110° C. for 24 h, calcined at 450° C. for 8 h, then mixed with 1.5 wt % (powder mass) of graphite and pressed into a 3×3 mm cylinder (3 mm in diameter and 3 mm in height) catalyst, about 200 g of Catalyst F was obtained. Based on the oxides, the catalyst contains 52% of copper oxide, 32% of silicon oxide, 10% of zinc oxide, 1% of cerium oxide and 5% of barium oxide.

For the remaining conditions, refer to Example 1.

Examples 7-12

Example 7 is basically the same as Example 1, except that the Gemini surfactant used in Example 7 was a Gemini surfactant with a structure of $C_{16-2-16}$, ethylenebis(hexadecyldimethylammonium bromide) (purchased from Henan Daochun Chemical Co., Ltd.).

Example 8 is basically the same as Example 2, except that the Gemini surfactant used in Example 8 was a Gemini surfactant with a structure of $C_{12-3-12}$, propylenebis(dodecyldimethylammonium bromide) (purchased from Henan Daochun Chemical Co., Ltd.).

Example 9 is basically the same as Example 3, except that the Gemini surfactant used in Example 9 was a Gemini surfactant with a structure of $C_{14-2-14}$, ethylenebis(tetradecyldimethylammonium bromide) (purchased from Henan Daochun Chemical Co., Ltd.).

Example 10 was basically the same as Example 4, except that the Gemini surfactant used in Example 10 was a Gemini surfactant with a structure of $C_{12-3-12}$, propylenebis(dodecyldimethylammonium bromide) (purchased from Henan Daochun Chemical Co., Ltd.).

Example 11 is basically the same as Example 5, except that the Gemini surfactant used in Example 11 was a Gemini surfactant with a structure of $C_{14\text{-}2\text{-}14}$, ethylenebis(tetradecyldimethylammonium bromide) (purchased from Henan Daochun Chemical Co., Ltd.).

Example 12 is basically the same as Example 6, except that the Gemini surfactant used in Example 12 was a Gemini surfactant with a structure of $C_{12\text{-}3\text{-}12}$, propylenebis(dodecyldimethylammonium bromide) (purchased from Henan Daochun Chemical Co., Ltd.).

Comparative Example 1

200 g of water was added to a reactor, and 60 g of fumed silica was added, and the mixture was stirred well. 332.2 g of copper nitrate was dissolved in 1.5 kg of water to prepare an aqueous solution of mixed salt, and an aqueous solution with 10 wt % sodium carbonate was prepared as a precipitant, and the two solutions were heated to 65° C. respectively. The coprecipitation method was used, the two solutions were added dropwise into the reactor at the same time, and the temperature in the reactor during the precipitation process was controlled at 65° C., the pH of the system was controlled at 7.0 and the reaction time was 1 h. After the addition was completed, the system was aged at 70° C. for 3 h, then filtered, washed, the filter cake was dried at 110° C. for 24 h, calcined at 450° C. for 8 h, then mixed with 1.2 wt % (powder mass) of graphite and pressed into a 3×3 mm cylinder (3 mm in diameter and 3 mm in height) catalyst, about 170 g of Catalyst G was obtained.

For the remaining conditions, refer to Example 1.

Comparative Example 2

332.2 g of copper nitrate and 292.4 g of zinc nitrate were dissolved in 1.65 kg of water to prepare an aqueous solution of mixed salt, sodium carbonate was dissolved in water to prepare an aqueous solution with 10 wt % sodium carbonate, and the two solutions were heated to 65° C. respectively. The coprecipitation method was used, the two solutions were added dropwise into the reactor at the same time, and the temperature in the reactor during the precipitation process was controlled at 65° C., the pH for precipitation was controlled at 7.0. After the precipitation was completed, the system was aged at 70° C. for 3h. After filtration and washing, 10.0 g of alumina was added to the filter cake, the treated filtered cake was dried at 110° C. for 12 h, calcined at 350° C. for 4 h, then mixed with 1.5 wt % (powder mass) of graphite, pressed and molded into a 3×3 mm cylinder (3 mm in diameter and 3 mm in height) catalyst, about 190 g of Catalyst H was obtained.

For the remaining conditions, refer to Example 1.

Comparative Example 3

During the preparation of the catalyst, no small molecular alcohol and Gemini surfactant were added, and the remaining conditions were the same as in Example 1. About 200 g of Catalyst I was obtained.

For the remaining conditions, refer to Example 1.

Comparative Example 4

During the preparation of the catalyst, no organic pore-forming agent PMMA was added, and the remaining conditions were the same as in Example 1. About 200 g of Catalyst J was obtained.

For the remaining conditions, refer to Example 1.

The results of the hydrogenation reaction of the catalysts of Examples 1-6 and the average copper ion contents in the hydrogenation solution are shown in Table 1, and the comparison of the catalysts before and after the reaction are shown in Table 2. The experimental results of the catalysts prepared in Examples 7-12 are basically the same as the corresponding experimental results of Examples 1-6 in sequence, in which the conversion rate of acetophenone were at least 98.1%, and the selectivity to α-phenylethanol were all at least 99.3%, the detection results of the average copper ion content in the hydrogenation solution were "not detected"; the side pressure strength of the catalysts before the reaction were all at least 188 N/particle, and the side pressure strength of the catalysts after the reaction were all at least 48.5 N/particle. The catalysts after the reaction were all complete without powdering and crushing.

TABLE 1

The results of the hydrogenation reaction and average copper ion content in the hydrogenation solution

|  | conversion rate of acetophenone % | selectivity to α-phenylethanol % | average copper ion content in the hydrogenation solution μg/g |
|---|---|---|---|
| Catalyst A | 98.1 | 99.4 | Not detected |
| Catalyst B | 99.3 | 99.3 | Not detected |
| Catalyst C | 98.8 | 99.4 | Not detected |
| Catalyst D | 98.9 | 99.5 | Not detected |
| Catalyst E | 98.6 | 99.3 | Not detected |
| Catalyst F | 99.2 | 99.5 | Not detected |
| Catalyst G | 86.0 | 97.5 | 38.2 |
| Catalyst H | 82.1 | 97.6 | 60.8 |
| Catalyst I | 92.6 | 98.7 | Not detected |
| Catalyst J | 93.1 | 98.5 | Not detected |

Note:
"Not detected" means the average copper ion content in the hydrogenation solution is <0.1 μg/g

TABLE 2

Comparison of the catalyst before and after the reaction

|  | catalyst before the reaction side pressure strength N/particle* | catalyst after the reaction side pressure strength N/particle | catalyst after the reaction state |
|---|---|---|---|
| Catalyst A | 188.1 | 48.5 | complete |
| Catalyst B | 210.9 | 65.9 | complete |
| Catalyst C | 220.6 | 68.1 | complete |
| Catalyst D | 192.3 | 54.4 | complete |
| Catalyst E | 205.7 | 62.3 | complete |
| Catalyst F | 198.3 | 58.9 | complete |
| Catalyst G | 163.2 | 15.7 | crushed |
| Catalyst H | 106.7 | could not be tested | powdered |
| Catalyst I | 195.7 | 55.3 | complete |
| Catalyst J | 198.2 | 58.5 | complete |

*N/particle is the unit of catalyst strength, which is the force applied for 1 catalyst to crush As can be seen from Tables 1 and 2, when using catalysts A to F, and catalysts I and J, no copper was detected in the hydrogenation solution, and the catalysts were complete and the side pressure strength of the catalysts were at least 30 N/particle after the reaction; however, as to the catalysts of Comparative Example 1 and Comparative Example 2, after the reaction, the catalysts were severely crushed and the side pressure strength of the catalysts were low. The catalyst H was powdered so that its side pressure strength could not be tested. ICP analysis showed that the copper content in the hydrogenation solution of the catalysts were high, indicating that the catalysts had significant loss. In addition, catalysts A to F have high activity and can effectively suppress side reactions such as hydrogenolysis to produce ethylbenzene and dehydration to produce styrene, and the catalysts of Comparative Examples 1 to 4 not only have low activity but also poor selectivity.

The invention claimed is:

1. A preparation method for a hydrogenation catalyst, comprising the following steps:
   (1) adding water, a small molecule alcohol, a Gemini surfactant and an organic pore-forming agent to a reactor, followed by adding a silica sol and stirring the mixture well to prepare an aqueous dispersion of silica sol containing the small molecule alcohol, the Gemini surfactant and the organic pore-forming agent;
   (2) dissolving a salt of a copper containing compound, a salt of a zinc containing compound, a salt of a rare-earth metal containing compound and a salt of an alkaline-earth metal containing compound in water to prepare a solution of mixed salt; dissolving a silicon containing alkaline precipitant and a silicon free alkaline precipitant in water to prepare an aqueous solution of alkaline precipitant; adding the solution of mixed salt and the aqueous solution of alkaline precipitant together to the aqueous dispersion of silica sol for reaction, with the pH of the reaction system during the reaction process being controlled at 5.0-9.0, and followed by aging to obtain a slurry;
   (3) filtering and washing the slurry to obtain a filter cake; and
   (4) drying, calcining and molding the filter cake to obtain the catalyst.

2. The preparation method according to claim 1, wherein the total amount of silicon in the catalyst is introduced together by the silica sol and the silicon containing alkaline precipitant, and the amount of silicon introduced by the silica sol accounts for 30-70 wt %, of the total amount of silicon in the catalyst.

3. The preparation method according to claim 2, wherein the amount of silicon introduced by the silica sol accounts for 35-65 wt % of the total amount of silicon in the catalyst; and
   the silica sol is an alkaline silica sol, with a pH value of 8.0-10.0.

4. The preparation method according to claim 1, wherein the silicon containing alkaline precipitant is a water soluble silicate;
   the silicon free alkaline precipitant is selected from the group consisting of potassium carbonate, sodium bicarbonate, potassium bicarbonate, sodium hydroxide, potassium hydroxide, ammonium carbonate, ammonium bicarbonate, carbamide and ammonia water and combinations thereof.

5. The preparation method according to claim 1, wherein the particle size of the organic pore-forming agent is less than 100 μm.

6. The preparation method according to claim 5, wherein the particle size of the organic pore-forming agent is 1-80 μm;
   the organic pore-forming agent is selected from the group consisting of PMMA, microcrystalline cellulose and methyl cellulose and combinations thereof.

7. The preparation method according to claim 1, wherein the amount of the organic pore-forming agent accounts for 0.5-20 wt % of the total weight of the catalyst.

8. The preparation method according to claim 1, wherein in step (1), the mass ratio of the small molecule alcohol to water is 1:20 to 1:10.

9. The preparation method according to claim 8, wherein the small molecule alcohol in step (1) is selected from the group consisting of methanol, ethanol, propanol and butanol and combinations thereof.

10. The preparation method according to claim 1, wherein the Gemini surfactant in the step (1) is added in an amount of 0.1%-1% of the total mass of the water and the small molecular alcohol.

11. The preparation method according to claim 10, wherein the Gemini surfactant is a bromide having a structure of $C_{m-n-m}$, wherein m is 12, 14, or 16, and n is 2, 3, 6, 8 or 10.

12. The preparation method according to claim 1, wherein the rare-earth metal is lanthanum and/or cerium; the alkaline-earth metal is selected from the group consisting of magnesium, calcium and barium and combinations thereof.

13. The preparation method according to claim 12, wherein the salt of the copper containing compound is selected from the group consisting of copper nitrate, copper chloride and copper acetate and combinations thereof; the salt of the zinc containing compound is selected from the group consisting of zinc nitrate, zinc chloride and zinc acetate and combinations thereof; the salt of the rare-earth metal compound is selected from the group consisting of nitrate, chloride and acetate and combinations thereof; the salt of alkaline-earth metal compound is selected from the group consisting of nitrate, chloride and acetate and combinations thereof.

14. The preparation method according to claim 1, wherein the temperature of the reaction process and the aging process in step (2) is 60-90° C.;
   in step (4), the calcining temperature is 300-700° C. and the calcining time is 4-12h.

15. The catalyst prepared by the preparation method according to claim 1; based on the total weight of the catalyst, the prepared catalyst contains 20-65 wt % of copper oxide, 15-50 wt % of silicon oxide, 2-25 wt % of zinc oxide, 0.1-5 wt % of rare-earth metal oxide and 0.5-15 wt % of alkaline-earth metal oxide.

16. The preparation method according to claim 15, wherein the prepared catalyst contains 40-63 wt % of copper oxide, 20-45 wt % of silicon oxide, 5-20 wt % of zinc oxide, 0.2-3 wt % of rare-earth metal oxide and 0.5-10 wt % of alkaline-earth metal oxide.

17. The preparation method according to claim 15, wherein the prepared catalyst contains 42-60 wt % of copper oxide, 22-40 wt % of silicon oxide, 10-18 wt % of zinc oxide, 0.5-2 wt % of rare-earth metal oxide and 1-5 wt % of alkaline-earth metal oxide.

18. A method for producing α-phenylethanol in the liquid phase hydrogenation of acetophenone, comprising contacting acetophenone with the catalyst prepared by the preparation method according to claim 1 in the presence of $H_2$ and recovering α-phenylethanol.

19. The method according to claim 18, wherein before catalyzing the hydrogenation of acetophenone to produce α-phenylethanol, the catalyst is reduced and activated;
   the reduction and activation of the catalyst includes the following steps: introducing a mixed gas of hydrogen and nitrogen with a volume fraction of $H_2$ not more than 10 v % while maintaining the volume space velocity of the mixed gas of hydrogen and nitrogen to be 300-1000 $h^{-1}$ to pre-reduce the catalyst for at least 0.5 h, followed by gradually increasing the proportion of hydrogen in mixed gas of hydrogen and nitrogen and controlling the hot spot temperature of the catalyst bed in this process to not exceed 220° C., and finally raising the temperature to 200-220° C. and reducing in a pure hydrogen atmosphere for 2-5 h to obtain an activated catalyst.

20. The method according to claim 19, wherein the contacting conditions for the hydrogenation of acetophenone to produce α-phenylethanol using the obtained activated catalyst include: a reaction pressure of 2.5-5 MPa, a reaction temperature of 70-140° C., a $H_2$/ACP molar ratio of 2-20:1 and a catalyst amount of 0.2-0.6 $g_{ACP} \cdot g_{cat}^{-1} \cdot h^{-1}$.

* * * * *